United States Patent
Wallace et al.

(10) Patent No.: US 9,198,713 B2
(45) Date of Patent: *Dec. 1, 2015

(54) ELECTRICAL MEANS TO NORMALIZE ABLATIONAL ENERGY TRANSMISSION TO A LUMINAL TISSUE SURFACE OF VARYING SIZE

(71) Applicant: COVIDIEN LP, Mansfield, MA (US)

(72) Inventors: Michael P. Wallace, Pleasanton, CA (US); Robert Garabedian, Mountain View, CA (US); Brent C. Gerberding, San Jose, CA (US)

(73) Assignee: Covidien LP, Masfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/299,535

(22) Filed: Jun. 9, 2014

(65) Prior Publication Data

US 2014/0288547 A1 Sep. 25, 2014

Related U.S. Application Data

(63) Continuation of application No. 12/143,404, filed on Jun. 20, 2008, now Pat. No. 8,784,338.

(60) Provisional application No. 60/936,865, filed on Jun. 22, 2007.

(51) Int. Cl.
*A61B 18/00* (2006.01)
*A61B 18/14* (2006.01)
(Continued)

(52) U.S. Cl.
CPC ............... *A61B 18/14* (2013.01); *A61B 5/053* (2013.01); *A61B 5/0538* (2013.01);
(Continued)

(58) Field of Classification Search
USPC .......................... 600/300, 560, 561, 587–595; 606/32–35; 607/115–138
See application file for complete search history.

(56) References Cited

U.S. PATENT DOCUMENTS

| | | |
|---|---|---|
| 552,832 A | 1/1896 | Fort |
| 3,901,241 A | 8/1975 | Allen, Jr. |

(Continued)

FOREIGN PATENT DOCUMENTS

| | | |
|---|---|---|
| DE | 3838840 | 5/1990 |
| DE | 4303882 | 8/1994 |

(Continued)

OTHER PUBLICATIONS

Castell, D. O. Gastroesophageal Reflux Disease: Current Strategies for Patient Management. Arch Fam Med. 1996; 5(4):221-227.

(Continued)

*Primary Examiner* — Sean Dougherty

(57) ABSTRACT

Methods and devices for measuring the size of a body lumen and a method for ablating tissue that uses the measurement to normalize delivery of ablational energy from an expandable operative element to a luminal target of varying circumference are provided. The method includes inserting into the lumen an expandable operative element having circuitry with resistivity or inductance that varies with circumference of the operative element, varying the expansion of the operative element with an expansion medium, measuring the resistivity of the circuitry, and relating the resistivity or inductance to a value for the circumference of the operative element. In some embodiments the sizing circuit includes a conductive elastomer wrapped around the operative element. Other embodiments apply to operative elements that include an overlapping energy delivery element support in which the overlap varies inversely with respect to the state of expansion, and electrodes that sense the amount of the overlap.

12 Claims, 7 Drawing Sheets

(51) Int. Cl.
  *A61B 5/053* (2006.01)
  *A61B 5/107* (2006.01)
  *A61B 18/02* (2006.01)
  *A61B 18/08* (2006.01)
  *A61B 18/18* (2006.01)
  *A61B 18/20* (2006.01)

(52) U.S. Cl.
  CPC .......... *A61B 5/1076* (2013.01); *A61B 18/1492* (2013.01); *A61B 18/0218* (2013.01); *A61B 18/082* (2013.01); *A61B 18/18* (2013.01); *A61B 18/20* (2013.01); *A61B 2018/00017* (2013.01); *A61B 2018/0022* (2013.01); *A61B 2018/00214* (2013.01); *A61B 2018/00488* (2013.01); *A61B 2018/00577* (2013.01); *A61B 2018/00642* (2013.01); *A61B 2018/00714* (2013.01); *A61B 2018/00755* (2013.01); *A61B 2018/00791* (2013.01); *A61B 2018/00875* (2013.01)

(56) References Cited

U.S. PATENT DOCUMENTS

| | | |
|---|---|---|
| 3,924,628 A | 12/1975 | Droegemueller et al. |
| 4,011,872 A | 3/1977 | Komiya |
| 4,304,239 A | 12/1981 | Perlin |
| 4,311,154 A | 1/1982 | Sterzer et al. |
| 4,407,298 A | 10/1983 | Lentz et al. |
| 4,411,266 A | 10/1983 | Cosman |
| 4,532,924 A | 8/1985 | Auth et al. |
| 4,565,200 A | 1/1986 | Cosman |
| 4,640,298 A | 2/1987 | Pless et al. |
| 4,658,836 A | 4/1987 | Turner |
| 4,662,383 A | 5/1987 | Sogawa et al. |
| 4,674,481 A | 6/1987 | Boddie, Jr. et al. |
| 4,676,258 A | 6/1987 | Inokuchi et al. |
| 4,765,331 A | 8/1988 | Petruzzi et al. |
| 4,776,349 A | 10/1988 | Nashef et al. |
| 4,860,744 A | 8/1989 | Johnson et al. |
| 4,887,614 A | 12/1989 | Shirakami et al. |
| 4,895,138 A | 1/1990 | Yabe |
| 4,907,589 A | 3/1990 | Cosman |
| 4,930,521 A | 6/1990 | Metzger et al. |
| 4,943,290 A | 7/1990 | Rexroth et al. |
| 4,947,842 A | 8/1990 | Marchosky et al. |
| 4,949,147 A | 8/1990 | Bacuvier |
| 4,955,377 A | 9/1990 | Lennox et al. |
| 4,966,597 A | 10/1990 | Cosman |
| 4,969,890 A | 11/1990 | Sugita et al. |
| 4,976,711 A | 12/1990 | Parins et al. |
| 4,979,948 A | 12/1990 | Geddes et al. |
| 4,998,539 A | 3/1991 | Delsanti |
| 5,006,119 A | 4/1991 | Acker et al. |
| 5,010,895 A | 4/1991 | Maurer et al. |
| 5,019,075 A | 5/1991 | Spears et al. |
| 5,035,696 A | 7/1991 | Rydell |
| 5,045,056 A | 9/1991 | Behl |
| 5,046,512 A | 9/1991 | Murchie |
| 5,047,028 A | 9/1991 | Qian |
| 5,056,532 A | 10/1991 | Hull et al. |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,100,423 A | 3/1992 | Fearnot |
| 5,106,360 A | 4/1992 | Ishiwara et al. |
| 5,117,828 A | 6/1992 | Metzger et al. |
| 5,122,137 A | 6/1992 | Lennox |
| 5,125,928 A | 6/1992 | Parins et al. |
| 5,151,100 A | 9/1992 | Abele et al. |
| 5,156,151 A | 10/1992 | Imran |
| 5,163,938 A | 11/1992 | Kambara et al. |
| 5,171,299 A | 12/1992 | Heitzmann et al. |
| 5,190,541 A | 3/1993 | Abele et al. |
| 5,197,963 A | 3/1993 | Parins |
| 5,197,964 A | 3/1993 | Parins |
| 5,215,103 A | 6/1993 | Desai |
| 5,236,413 A | 8/1993 | Flering |
| 5,242,441 A | 9/1993 | Avitall |
| 5,255,679 A | 10/1993 | Imran |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,169 A | 1/1994 | Afromowitz et al. |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,438 A | 5/1994 | Shturman |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,375,594 A | 12/1994 | Cueva |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,397,308 A * | 3/1995 | Ellis et al. ............... 604/100.03 |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,411,025 A | 5/1995 | Webster, Jr. |
| 5,413,573 A | 5/1995 | Koivukangas |
| 5,415,657 A | 5/1995 | Taymor-Luia |
| 5,421,819 A | 6/1995 | Edwards et al. |
| 5,423,808 A | 6/1995 | Edwards et al. |
| 5,423,812 A | 6/1995 | Ellman et al. |
| 5,425,704 A | 6/1995 | Sakurai et al. |
| 5,428,658 A | 6/1995 | Oettinger et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,454,809 A | 10/1995 | Janssen |
| 5,456,662 A | 10/1995 | Edwards et al. |
| 5,456,682 A | 10/1995 | Edwards et al. |
| 5,458,571 A | 10/1995 | Lampropoulos et al. |
| 5,458,596 A | 10/1995 | Lax et al. |
| 5,458,597 A | 10/1995 | Edwards et al. |
| 5,462,545 A | 10/1995 | Wang et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |

(56) References Cited

U.S. PATENT DOCUMENTS

| | | |
|---|---|---|
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,517,989 A | 5/1996 | Frisbie et al. |
| 5,520,684 A | 5/1996 | Imran |
| 5,522,815 A | 6/1996 | Burgin, Jr. et al. |
| 5,524,622 A | 6/1996 | Wilson |
| 5,531,676 A | 7/1996 | Edwards et al. |
| 5,531,677 A | 7/1996 | Lundquist et al. |
| 5,533,515 A | 7/1996 | Coller |
| 5,533,958 A | 7/1996 | Wilk |
| 5,536,240 A | 7/1996 | Edwards et al. |
| 5,536,267 A | 7/1996 | Edwards et al. |
| 5,540,655 A | 7/1996 | Edwards et al. |
| 5,542,916 A | 8/1996 | Hirsch et al. |
| 5,542,928 A | 8/1996 | Evans et al. |
| 5,549,644 A | 8/1996 | Lundquist et al. |
| 5,549,661 A | 8/1996 | Korkis et al. |
| RE35,330 E | 9/1996 | Malone et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,566,221 A | 10/1996 | Smith et al. |
| 5,569,241 A | 10/1996 | Edwards |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,591,195 A | 1/1997 | Taheri et al. |
| 5,599,345 A | 2/1997 | Edwards et al. |
| 5,609,151 A | 3/1997 | Mulier et al. |
| 5,621,780 A | 4/1997 | Smith et al. |
| 5,624,439 A | 4/1997 | Edwards et al. |
| 5,651,780 A | 7/1997 | Jackson et al. |
| 5,651,788 A | 7/1997 | Fleischer et al. |
| 5,658,278 A | 8/1997 | Imran et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,942 A | 2/1998 | Stern et al. |
| 5,716,410 A | 2/1998 | Wang et al. |
| 5,720,293 A | 2/1998 | Quinn et al. |
| 5,730,128 A | 3/1998 | Pomeranz et al. |
| 5,732,698 A | 3/1998 | Swanson et al. |
| 5,738,096 A | 4/1998 | Ben-Haim |
| 5,748,699 A | 5/1998 | Smith |
| 5,752,522 A | 5/1998 | Murphy |
| 5,769,846 A | 6/1998 | Edwards et al. |
| 5,769,880 A | 6/1998 | Truckai et al. |
| 5,779,698 A | 7/1998 | Clayman et al. |
| 5,795,325 A * | 8/1998 | Valley ............... A61B 17/12022 604/103.1 |
| 5,797,835 A | 8/1998 | Green |
| 5,797,903 A | 8/1998 | Swanson et al. |
| 5,800,334 A | 9/1998 | Wilk |
| 5,800,429 A | 9/1998 | Edwards |
| 5,807,261 A | 9/1998 | Benaron et al. |
| 5,820,629 A | 10/1998 | Cox |
| 5,823,197 A | 10/1998 | Edwards |
| 5,823,955 A | 10/1998 | Kuck et al. |
| 5,827,273 A | 10/1998 | Edwards |
| 5,830,129 A | 11/1998 | Baer et al. |
| 5,830,213 A | 11/1998 | Panescu et al. |
| 5,833,688 A | 11/1998 | Sieben et al. |
| 5,836,874 A | 11/1998 | Swanson et al. |
| 5,842,984 A | 12/1998 | Avitall |
| 5,846,196 A | 12/1998 | Siekmeyer et al. |
| 5,860,974 A | 1/1999 | Abele |
| 5,861,036 A | 1/1999 | Godin |
| 5,863,291 A | 1/1999 | Schaer |
| 5,871,483 A | 2/1999 | Jackson et al. |
| 5,876,340 A | 3/1999 | Tu et al. |
| 5,888,743 A | 3/1999 | Das |
| 5,891,134 A | 4/1999 | Goble et al. |
| 5,895,355 A | 4/1999 | Schaer |
| 5,902,263 A | 5/1999 | Patterson et al. |
| 5,902,308 A | 5/1999 | Murphy |
| 5,904,711 A | 5/1999 | Flom |
| 5,925,044 A | 7/1999 | Hofmann et al. |
| 5,938,694 A | 8/1999 | Jaraczewski et al. |
| 5,964,755 A | 10/1999 | Edwards |
| 5,976,129 A | 11/1999 | Desai |
| 5,984,861 A | 11/1999 | Crowley |
| 5,997,534 A | 12/1999 | Tu et al. |
| 6,006,755 A | 12/1999 | Edwards |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson et al. |
| 6,027,499 A | 2/2000 | Johnston et al. |
| 6,033,397 A | 3/2000 | Laufer et al. |
| 6,039,701 A | 3/2000 | Silwa et al. |
| 6,041,260 A | 3/2000 | Stern et al. |
| 6,044,846 A | 4/2000 | Edwards |
| 6,053,172 A | 4/2000 | Hovda et al. |
| 6,053,913 A | 4/2000 | Tu et al. |
| 6,056,744 A | 5/2000 | Edwards |
| 6,059,719 A | 5/2000 | Yamamoto et al. |
| 6,068,629 A | 5/2000 | Haissaguerre et al. |
| 6,071,277 A | 6/2000 | Farley et al. |
| 6,073,052 A | 6/2000 | Zelickson et al. |
| 6,086,558 A | 7/2000 | Bower et al. |
| 6,091,993 A | 7/2000 | Bouchier et al. |
| 6,091,995 A | 7/2000 | Ingle et al. |
| 6,092,528 A | 7/2000 | Edwards |
| 6,095,966 A | 8/2000 | Chornenky et al. |
| 6,096,054 A | 8/2000 | Wyzgala et al. |
| 6,102,908 A | 8/2000 | Tu et al. |
| 6,112,123 A | 8/2000 | Kelleher et al. |
| 6,120,434 A | 9/2000 | Kimura et al. |
| 6,123,703 A | 9/2000 | Tu et al. |
| 6,123,718 A | 9/2000 | Tu et al. |
| 6,138,046 A | 10/2000 | Dalton |
| 6,142,994 A | 11/2000 | Swanson et al. |
| 6,146,149 A | 11/2000 | Daound |
| 6,149,647 A | 11/2000 | Tu et al. |
| 6,162,237 A | 12/2000 | Chan |
| 6,179,836 B1 | 1/2001 | Eggers et al. |
| 6,182,666 B1 | 2/2001 | Dobak, III |
| 6,183,468 B1 | 2/2001 | Swanson et al. |
| 6,197,022 B1 | 3/2001 | Baker |
| 6,237,355 B1 | 5/2001 | Li |
| 6,238,392 B1 | 5/2001 | Long |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,273,886 B1 | 8/2001 | Edwards et al. |
| 6,321,121 B1 | 11/2001 | Zelickson et al. |
| 6,325,798 B1 | 12/2001 | Edwards et al. |
| 6,325,800 B1 | 12/2001 | Durgin et al. |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,363,937 B1 | 4/2002 | Hovda et al. |
| 6,383,181 B1 | 5/2002 | Johnston et al. |
| 6,394,949 B1 | 5/2002 | Crowley et al. |
| 6,402,744 B2 | 6/2002 | Edwards et al. |
| 6,405,732 B1 | 6/2002 | Edwards et al. |
| 6,409,723 B1 | 6/2002 | Edwards |
| H2037 H | 7/2002 | Yates et al. |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Durgin et al. |
| 6,440,128 B1 | 8/2002 | Edwards et al. |

(56) References Cited

U.S. PATENT DOCUMENTS

| | | |
|---|---|---|
| 6,448,658 B2 | 9/2002 | Takata et al. |
| 6,451,014 B1 | 9/2002 | Wakikaldo et al. |
| 6,454,790 B1 | 9/2002 | Neuberger et al. |
| 6,464,697 B1 | 10/2002 | Edwards |
| 6,468,272 B1 | 10/2002 | Koblish et al. |
| 6,514,246 B1 | 2/2003 | Swanson |
| 6,514,249 B1 | 2/2003 | Maguire et al. |
| 6,535,768 B1 | 3/2003 | Baker et al. |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1 | 4/2003 | Rosinko et al. |
| 6,551,310 B1 | 4/2003 | Ganz |
| 6,551,315 B2 | 4/2003 | Kortenbach et al. |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,639 B1 | 6/2003 | Ingle et al. |
| 6,575,966 B2 | 6/2003 | Lane et al. |
| 6,589,238 B2 | 7/2003 | Edwards et al. |
| 6,613,047 B2 | 9/2003 | Edwards |
| 6,641,581 B2 | 11/2003 | Muzzammel |
| 6,663,626 B2 | 12/2003 | Truckai et al. |
| 6,673,070 B2 | 1/2004 | Edwards et al. |
| 6,682,528 B2 | 1/2004 | Frazier et al. |
| 6,695,764 B2 | 2/2004 | Silverman et al. |
| 6,712,074 B2 | 3/2004 | Edwards et al. |
| 6,712,814 B2 | 3/2004 | Edwards et al. |
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,860,878 B2 | 3/2005 | Brock |
| 6,866,663 B2 | 3/2005 | Edwards et al. |
| 6,872,206 B2 | 3/2005 | Edwards et al. |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,048,734 B1 | 5/2006 | Fleischman et al. |
| 7,056,320 B2 | 6/2006 | Utley et al. |
| 7,083,620 B2 | 8/2006 | Jahns et al. |
| 7,089,063 B2 | 8/2006 | Lesh et al. |
| 7,122,031 B2 | 10/2006 | Edwards et al. |
| 7,125,407 B2 | 10/2006 | Edwards et al. |
| 7,150,745 B2 | 12/2006 | Stern |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,293,563 B2 | 11/2007 | Utley et al. |
| 7,316,652 B2 | 1/2008 | Dalgaard |
| 7,326,207 B2 | 2/2008 | Edwards |
| 7,329,254 B2 | 2/2008 | West et al. |
| 7,416,549 B2 | 8/2008 | Young et al. |
| 7,425,212 B1 | 9/2008 | Danek et al. |
| 7,680,543 B2 | 3/2010 | Azure |
| 7,850,685 B2 | 12/2010 | Kunis et al. |
| 8,273,012 B2 | 9/2012 | Wallace |
| 8,398,631 B2 | 3/2013 | Ganz |
| 8,585,594 B2 * | 11/2013 | Forster et al. .......... 600/437 |
| 8,646,460 B2 | 2/2014 | Utley |
| 8,702,695 B2 | 4/2014 | Wallace |
| 2001/0041887 A1 | 11/2001 | Crowley |
| 2001/0051802 A1 | 12/2001 | Woloszko et al. |
| 2002/0087151 A1 | 7/2002 | Mody |
| 2002/0128650 A1 | 9/2002 | McClurken |
| 2002/0177847 A1 | 11/2002 | Long |
| 2002/0183739 A1 | 12/2002 | Long |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1 | 8/2003 | Ganz et al. |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0082947 A1 | 4/2004 | Oral |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0187546 A1 | 8/2005 | Bek et al. |
| 2005/0215983 A1 | 9/2005 | Brock |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edward et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0095032 A1 | 5/2006 | Jackson et al. |
| 2006/0106321 A1 * | 5/2006 | Lewinsky .......... A61B 5/02007 600/491 |
| 2006/0247614 A1 | 11/2006 | Sampson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118106 A1 | 5/2007 | Utley et al. |
| 2007/0118159 A1 | 5/2007 | Deem et al. |
| 2007/0135809 A1 | 6/2007 | Utley et al. |
| 2007/0142831 A1 | 6/2007 | Shadduck |
| 2007/0167963 A1 | 7/2007 | Deem et al. |
| 2007/0219570 A1 | 9/2007 | Deem et al. |
| 2007/0255296 A1 | 11/2007 | Sauer |
| 2007/0276361 A1 | 11/2007 | Stevens-Wright et al. |
| 2007/0287994 A1 | 12/2007 | Patel |
| 2007/0288001 A1 | 12/2007 | Patel |
| 2008/0097427 A1 | 4/2008 | Stern et al. |
| 2008/0275445 A1 | 11/2008 | Kelly et al. |
| 2008/0319350 A1 | 12/2008 | Wallace |
| 2009/0012512 A1 | 1/2009 | Utley et al. |
| 2009/0012513 A1 | 1/2009 | Utley et al. |
| 2009/0012518 A1 | 1/2009 | Utley et al. |
| 2009/0036733 A1 | 2/2009 | Wallace |
| 2009/0048593 A1 | 2/2009 | Ganz |
| 2009/0177194 A1 | 7/2009 | Wallace |
| 2009/0187181 A1 | 7/2009 | Shadduck |
| 2009/0299355 A1 | 12/2009 | Bencini et al. |
| 2009/0318914 A1 | 12/2009 | Utley |
| 2010/0063495 A1 | 3/2010 | Utley et al. |
| 2010/0191237 A1 | 7/2010 | Shadduck |
| 2010/0234840 A1 | 9/2010 | Jackson et al. |

(56) References Cited

U.S. PATENT DOCUMENTS

| | | |
|---|---|---|
| 2011/0270249 A1 | 11/2011 | Utley et al. |
| 2012/0004654 A1 | 1/2012 | Jackson et al. |
| 2012/0004656 A1 | 1/2012 | Jackson |
| 2012/0239028 A1 | 9/2012 | Wallace |
| 2013/0123694 A1* | 5/2013 | Subramaniyan ..... A61B 5/6853 604/100.01 |

FOREIGN PATENT DOCUMENTS

| | | |
|---|---|---|
| EP | 0105677 | 4/1984 |
| EP | 0115420 | 8/1984 |
| EP | 0139607 | 5/1985 |
| EP | 0251745 | 1/1988 |
| EP | 0521595 A2 | 1/1993 |
| EP | 0608609 | 8/1994 |
| EP | 1323382 A1 | 7/2003 |
| EP | 1634542 B1 | 3/2006 |
| JP | 8506738 | 7/1996 |
| JP | 2005503181 | 2/2005 |
| WO | 9101773 | 2/1991 |
| WO | 9103207 A1 | 3/1991 |
| WO | 9210142 | 6/1992 |
| WO | 9308755 | 5/1993 |
| WO | 9407446 A1 | 4/1994 |
| WO | 9410925 | 5/1994 |
| WO | 9421165 | 9/1994 |
| WO | 9422366 | 10/1994 |
| WO | 9426178 | 11/1994 |
| WO | 9518575 | 7/1995 |
| WO | 9519142 | 7/1995 |
| WO | 9525472 | 9/1995 |
| WO | 9600042 | 1/1996 |
| WO | 9616606 | 6/1996 |
| WO | 9629946 | 10/1996 |
| WO | 9704702 | 2/1997 |
| WO | 9706857 | 2/1997 |
| WO | 9732532 | 9/1997 |
| WO | 9743971 | 11/1997 |
| WO | 9812999 A2 | 4/1998 |
| WO | 9814238 A1 | 4/1998 |
| WO | 9818393 A1 | 5/1998 |
| WO | 9903413 | 1/1999 |
| WO | 9935987 | 7/1999 |
| WO | 9942046 | 8/1999 |
| WO | 9955245 | 11/1999 |
| WO | 0001313 | 1/2000 |
| WO | 0059393 | 10/2000 |
| WO | 0062699 A2 | 10/2000 |
| WO | 0066017 A1 | 11/2000 |
| WO | 0066021 | 11/2000 |
| WO | 0066052 A1 | 11/2000 |
| WO | 0069376 | 11/2000 |
| WO | 0122897 A1 | 4/2001 |
| WO | 0135846 | 5/2001 |
| WO | 0145550 A2 | 6/2001 |
| WO | 0189440 | 11/2001 |
| WO | 02096327 A2 | 12/2002 |
| WO | 03070091 A1 | 8/2003 |
| WO | 2004043280 A1 | 5/2004 |
| WO | 2007001981 A2 | 1/2007 |
| WO | 2007061984 A2 | 5/2007 |

OTHER PUBLICATIONS

Dallamagne et al; Laparoscopic Nissen Fundoplication: Preliminary. Surgical Laparoscopy and Endoscopy. 1991; 1(3):138-143.

Hinder et al.; the Technique of Laparoscopic Nissen Fundoplication. Surgical Laparoscopy and endoscopy. 1992; 2(3): 265-272.

Kaneko et al; Physiological Laryngeal Pacemaker. Trans Am Soc. Artif Intern Organs. 1985; XXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K. A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, Chapter 21. 1985; 263-279.

Reynolds, J.C. Influence of Pathophysiology, Severity, and Cost on the Medical Management of Gastroesophageal Reflex Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. raven Press. 1988; 75-102.

Rice et al; Endoscopic Paranasal Sinus Surgery. Chapter 6, total Endoscopic Sphenoethmoidectomy. The Technique of Wigand. Raven Press. 1988; 103-125.

Salameh et al; An Animal Model Study to Clarify and Investigate Endoscopic Tissue Coagulation by Using a New Monopolar Device. Gastrointestinal Endoscopy; 2004; 59(1): 107-112.

Urshal, J. D. Complications of Antireflux Surgery. Am J. Surg. 1993; 166(1):68-70.

* cited by examiner

ELECTRICAL MEANS TO NORMALIZE ABLATIONAL ENERGY TRANSMISSION TO A LUMINAL TISSUE SURFACE OF VARYING SIZE

CROSS REFERENCE TO RELATED APPLICATIONS

This application is a continuation of U.S. patent application Ser. No. 12/143,404, filed Jun. 20, 2008, entitled, "ELECTRICAL MEANS TO NORMALIZE ABLATIONAL ENERGY TRANSMISSION TO A LUMINAL TISSUE SURFACE OF VARYING SIZE," which claims priority to U.S. provisional patent application No. 60/936,865, entitled "ELECTRICAL MEANS TO ESTIMATE DIAMETER MEASUREMENTS AND AN UNFURLING ELECTRODE CONCEPT TO ADAPT TO ANY BODY ORIFICE," filed on Jun. 22, 2007, each of which are incorporated by reference in their entirety for all purposes.

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD OF THE INVENTION

The present invention relates generally to medical methods and systems for treatment of body lumens. More particularly, the invention is directed determining physiologic characteristics of body lumens such as the esophagus in preparation for medical treatment such as ablational therapy.

BACKGROUND OF THE INVENTION

The human body has a number of internal body lumens, as in the gastrointestinal tract, with an inner lining or layer that can be susceptible to disease. As an example, gastroesophageal reflux disease (GERD), which involves inappropriate relaxation of the lower esophageal sphincter, manifests with symptoms of heartburn and regurgitation of gastric and intestinal contents. Patients with severe forms of gastroesophageal reflux disease can sometimes develop secondary damage of the esophagus due to the interaction of gastric or intestinal contents with esophageal cells not designed to experience such interaction.

The esophagus is composed of three primary tissue layers; a superficial mucosal layer lined by squamous epithelial cells, a middle submucosal layer and a deeper muscle layer. When gastroesophageal reflux occurs, the superfacial squamous epithelial cells are exposed to gastric acid, along with intestinal bile acids and enzymes. This exposure may be tolerated, but in some cases can lead to a condition known's as Barrett's esophagus, in which damage and alteration of the squamous cells causes them to change into taller, specialized columnar epithelial cells. Barrett's esophagus has important clinical consequences, as the columnar cells can become dysplastic, and then further progress to adenocarcinoma of the esophagus.

Accordingly, attention has been focused on identifying and removing this abnormal Barrett's columnar epithelium in order to mitigate more severe implications for the patient. Devices and methods for treating abnormal body tissue by application of various forms of energy to such tissue have been described, such as radio frequency ablation. However, precise control of the depth of penetration of the energy means, these methods and devices is critical to the success of such ablational therapy. Uncontrolled energy application can penetrate too deeply into the esophageal wall, beyond the mucosa and submucosal layers, into the muscularis externa, potentially causing esophageal perforation, stricture or bleeding. Among the factors and information needed for administration of the correct amount of treatment energy to the tissue is knowledge of the size of the esophagus and area to be treated.

Medical procedures for treating Barrett's esophagus typically involve deployment of an expandable catheter inside the esophagus. Expandable catheters are preferred because the profile of the catheter is ideally as small as possible to allow for ease of delivery, while treatment of the esophagus is most efficiently performed when the catheter is at or slightly larger than the diameter of the esophageal wall. Proper sizing and/or pressurization of the delivery device is desirable to prevent over-distension of the organ, which can result in harm to the organ, or under-expansion of the catheter, which can results in incomplete treatment. Accordingly, accurate and simple measurement of the size of the lumen and control of the pressure of the catheter on the lumen surface promotes the proper engagement and delivery of energy to the luminal wall so that a uniform and controlled depth of treatment can be administered.

Ablational devices typically need to make an appropriate and reproducible therapeutic contact between an ablational surface and the surface of a tissue area targeted for ablation. A number of ablational devices and methods for using them have been described in US patents and applications (U.S. Pat. No. 6,551,310 of Ganz issued on Apr. 22, 2003, application Ser. No. 10/370,645 of Ganz published as US2003/0158550 on Aug. 21, 2003, application Ser. No. 10/426,923 of Stern published as US2004/0087936 on May 6, 2004, application Ser. No. 10/754,452 of Jackson published as US2004/0215235 on Oct. 28, 2004, application Ser. No. 10/754,445 of Ganz published as US2004/0215296 on Oct. 28, 2004, application Ser. No. 11/244,385 of Jackson published as US2006/0095032 on May 4, 2006, and application Ser. No. 11/633,938 of Jackson published as US2007/0100333 on May 3, 2007) that make use of an expandable balloon to exert pressure from behind the ablational surface to press it against the target tissue area. Inasmuch as the inner diameter of luminal organs, such as gastrointestinal organs, vary in size, the extent or volume to which a balloon is inflated to achieve therapeutic contact will vary accordingly.

One currently available approach to creating consistency in the pressure that supports an appropriate or desirable level of therapeutic contact is to pre-test the target ablation site in order to know what inflated air volume is appropriate. Accordingly, measurements may be taken while pressurizing an oversized balloon to a specific pressure (for example, 4 psig) and then used to estimate the diameter of the esophagus, as described in U.S. patent application Ser. No. 11/244,385 of Jackson, published as US 2006/0095032. While this technique works well under ideal circumstances, in practical circumstances, leaks in the system can cause the production of inaccurate diameter estimates. Preventing leaks has been shown to be difficult as there are various locations in the system where a leak may occur.

Therefore, there is a need for alternative means of measuring the diameter or circumference of a body lumen in anticipation of a treatment, such as an ablation. This disclosure describes alternative devices and methods of accomplishing this task.

SUMMARY OF THE INVENTION

The present invention comprises methods and systems for sizing a body lumen, such as the esophagus. The sizing of a body lumen can provide information that is useful for determining values for various parameters of therapeutic treatments as exemplified by ablation treatment, such as normalizing the energy density delivered from an ablating surface to a tissue surface. Although the following description focuses on exemplary embodiments configured for treatment of the esophagus, other embodiments may be used to treat any other suitable lumen in the body. Further, although ablational treatment is described as an exemplary therapeutic treatment, the invention may be applied to any form of therapeutic treatment in which it is beneficial to normalize the delivery of treatment to the size of a lumen being treated. In particular, the methods and systems of the present invention may be used whenever accurate measurement of a body lumen or uniform delivery of energy is desired to treat a controlled depth of tissue in a lumen or cavity of the body, especially where such body structures may vary in size.

Embodiments of the invention relate to methods of measuring the size of a body lumen, as for example an inner circumference, devices for measuring such a lumen, and methods for ablating targeted tissue in a body lumen that make use of the size measurement to control the delivery of ablative energy. The inner circumference may be considered the parameter most directly measured by the method, as sensing elements are arranged linearly along a surface aligned with the circumference of the lumen, but such measurements may also be related directly to diameter and cross-sectional surface area of the lumen, as such values may be beneficial in some applications. Further, by a calculation that includes a longitudinal measure of a portion of the lumen, values may be calculated for a luminal surface area, as may be treated, for example, by an ablational device. Still further, if treatment is being directed to a fractional portion of the circumference of a lumen, those surface area values can be calculated as well.

Measuring the size of a body lumen, as exemplified by a measure of the inner circumference of a body lumen includes expanding the size of an operative element within the lumen, the operative element having sensing circuitry with resistivity that varies according to the size of the operative element, varying the sensing circuitry in accordance with the expansion of the operative element, measuring the resistivity of the sensing circuitry, determining the size of the lumen based on the measuring step. This summary will focus on resistivity as the exemplary feature of the circuitry that varies in accordance with the size of the operative element of the lumen it occupies, but all that which is said with regard to resistivity may be applied to inductance as well. Embodiments that make use of inductance will, however, be briefly summarized further below.

Varying the size of the operative element, for example by expanding it, may be performed by expanding an inflatable balloon within the operative element, and may include expanding the size of the operating element to exert a predetermined pressure on the lumen. The expansion medium may be either a liquid or a gas. In some embodiments, the pressure is typically between about 1 psig and about 7 psig; in some embodiments it is between about 3 psig and about 5 psig, and in particular embodiments the pressure is about 4 psig. In some embodiments of the method, varying the degree of expansion of the operative element includes automatically inflating and/or deflating a balloon. These pressures have been determined to be appropriate for effecting a coaptive ablation of gastrointestinal luminal walls. In embodiments of the invention that are directed toward other target sites or directed toward other types of treatment with other objectives, other pressures may be beneficial and are included as embodiments of the method.

In some embodiments of the method, varying or expanding the size of the operative element includes expanding the size of the operative element to achieve a predetermined resistivity of the size-sensing circuitry included within the operative element. In some embodiments, the circuitry includes size-sensing elements that include points of electrical contact. In other embodiments, the circuitry may include size-sensing elements that have any one or more of brush elements, optical sensors, magnetic contact points, or electro-mechanical contact points.

In some embodiments of the method, varying the size-sensing circuitry includes or causes stretching a conductive elastomer that is included within the circuit, the conductive elastomer being wrapped around at least a portion of the expandable operative element, the resistivity of the conductive elastomer increasing as it stretches in accordance with the expansion of the size of the operative element.

In other embodiments of the method, expanding the operative element includes decreasing an area of overlap between two longitudinal edges of a circumferentially-expandable energy delivery support having two longitudinal edges that overlap each other, the amount of overlap between the two edges decreasing in accordance with the size of the operative element expanding. In these embodiments, decreasing the area of overlap between the two edges of the energy delivery support varies the sensing circuitry, such circuitry being formed by sensing elements that arranged on both edges of the energy delivery support in the region of overlap, the resistance of the formed circuitry varying in accordance with the amount of the area of overlap.

Some embodiments of the method may include more than one approach to sizing the lumen by varying the sensing circuitry as have been summarized. For example, some embodiments may make use both of size-sensing circuitry that includes a conductive elastomer as well as circuitry that is responsive to changes in the amount of overlap of two ablational element delivery support edges.

Embodiments of the invention include devices for measuring the size of a body lumen, as for example the circumference of the body lumen as reflected in the circumference of an expandable operative element that is expanded within the lumen. Such devices include an expandable operative element having a circuitry whose resistivity (or inductance) varies according to the size, the circumference, for example, of the operative element. Some embodiments of the device include an inflatable balloon that is substantially responsible for expanding the operative element, but other embodiments may include operative elements that expand by mechanical means that are equally capable of exerting pressure against a lumen.

In some embodiments of the device, the operative element further includes one or more energy delivery elements, as for example, radiofrequency delivery elements to effect an ablation treatment on target tissue. These energy delivery elements may include a radiofrequency electrode, an array of electrodes, or solid-state circuitry. In various embodiments, the ablative energy elements may be arranged directly on the expandable balloon, or arranged on an electrode support that is itself engaged around the balloon. In other embodiments, alternative forms of energy and appropriate delivery elements may be included, such as microwave energy emanating from an antenna, light energy emanating from photonic elements, thermal energy transmitted conductively from heated ablational structure surfaces or as conveyed directly to tissue by heated gas or liquid, or a heat-sink draw of energy, as provided by cryonic cooling of ablational structure surfaces, or as applied by direct cold gas or fluid contact with tissue.

In some embodiments of the device, the circuitry includes a portion of a band of conductive elastomer wrapped around a circumferentially expandable portion of the operative element, such as around an inflatable balloon, such that when the balloon is contracted, the length of the conductive elastomer band is contracted, and when the balloon is expanded, the length of the conductive elastomeric band is expanded. In other embodiments, the device includes an ablational energy delivery element support arranged around the balloon, and the band of conductive elastomer is wrapped around the support. The conductive elastomeric portion of size sensing circuits of these embodiments is configured to relate size-sensing data by virtue of the electrical properties such as resistivity or inductance that vary according to the degree of contraction or stretch of the conductive elastomer.

Embodiments of circuitry that include a conductive elastomer within a size-sensing circuit thus depend on the particular construction of the device. For example, the conductive elastomer may be wrapped around an expandable member included within the operative element, such as an inflatable balloon. In some embodiments, treatment delivery elements such as ablation energy delivery elements may be arranged directly on the balloon, and in other embodiments, an intervening ablation energy delivery element support carrying the energy delivery elements may be wrapped around the balloon. In all these embodiments, a conductive elastomer may be wrapped around any portion of the operative element that expands in a manner that accords with the circumferential expansion of the operative device as a whole. In still other embodiments, the conductive elastomer may be applied to an internal surface of the balloon, or the internal surface of any portion of the operative element that expands in a manner that accords with the circumferential expansion of the operative device as a whole.

In other embodiments of the device, as noted above, the device includes an ablational energy delivery element support arranged around an inflatable balloon. The support of these device embodiments has a first edge and a second edge that mutually overlap each other, and the support is circumferentially expandable by the balloon such that when the balloon is contracted an area of mutual overlap of the two edges is inversely related to the amount of expansion of the balloon. For example, when the balloon is contracted or not expanded, the area of mutual overlap is relatively large, and when the balloon is expanded, the area of mutual overlap of the two edges is relatively small. In these embodiments, the circuitry includes size sensing elements on both edges of the overlapping support; such elements are configured to make an electrical connection across the area of mutual overlap to form a circuit with a particular resistivity, and the elements are also configured such that the particular circuit-forming electrical connection between sensing elements varies according to the amount of mutual overlap of the two edges.

In these device embodiments, configuration of the sensing elements and their pattern or distribution between the two longitudinal edges of an ablational energy delivery support may take various forms; three exemplary embodiments will be summarized. In some embodiments of the device, the first edge includes a single size-sensing element and the second edge includes a plurality of spaced-apart size-sensing elements, the particular element among the plurality of elements on the second edge that makes a connection to the element on the first edge varies according the amount of mutual overlap of the two edges, and the resistivity of circuit thus formed varies according to which of the elements on the second edge is included in the circuit. In other embodiments of the device, the first edge includes a single sensing element and the second edge includes a plurality of closely-spaced sensing elements, the elements configured such that the element on the first edge can make a connection with one of the plurality of the elements on the second edge or with two adjacent elements, and the resistivity of circuit formed varies according to which one or which two of the elements on the second edge are included in the circuit. In still other embodiments of the device, the first edge includes a single sensing element and the second edge includes an elongated sensing element; the elements are configured such that the single element on the first edge forms a circuit by making contact with the elongated element on the second edge at a point that varies along its length, thereby creating a circuit of varying length, and the resistivity of the circuit varies according to the length of the element on the second edge that is included in the circuit. All three of these approaches provide data from the size-sensing elements that relates to the size of the operative element in real time.

Embodiments of the invention further include methods for ablating target tissue in a body lumen. These methods basically include sizing steps as have been summarized that are coupled with the delivery of ablation energy at a level that is normalized per the sizing data provided by the sizing steps. The method includes inserting an expandable operative element into the lumen, the operative element having sensing circuitry with resistivity that varies according to the size of the operative element, expanding the operative element to contact the target tissue at a predetermined pressure, varying the sensing circuitry in accordance with the expansion of the operative element, measuring the resistivity of the sensing circuitry, determining the size of the lumen based on the measuring step, and controlling the delivery of energy to the operative element according to the size of the lumen.

Controlling delivery of energy may manifest or be expressed in terms of delivery of energy to the operative element, or in terms of delivery of energy from the operative element to the tissue. Further, ablation may be controlled in terms of energy, power, or power density as it is normalized to target tissue surface area. Thus, embodiments of the method make may use of an operative element that includes an expandable balloon for expanding the operative element, an ablational energy delivery surface for ablating tissue, and circuitry with a variable resistivity for measuring the circumference of the operative element.

In some embodiments of the method, controlling delivery of energy includes delivering energy in proportion to the surface area of the targeted tissue with which the operative element is in contact. In various embodiments of the method, controlling delivery of energy includes controlling delivery of energy from the operative element into the tissue, and more specifically, may include controlling the depth to which tissue is ablated.

In various embodiments of the method, controlling delivery of energy includes controlling an amount of power delivered to the tissue over time, and more specifically may include normalizing power delivered to the tissue over time. In various embodiments of the method, controlling delivery of energy includes controlling an amount of energy delivered to the tissue over time, and may include controlling delivered energy density. In other embodiments of the method, controlling delivery of energy includes monitoring and controlling tissue impedance over time, or controlling delivery of energy includes monitoring and controlling tissue temperature over time.

In other embodiments of the method, controlling delivery of energy may further include controlling an amount of power delivered to the tissue by rapidly increasing the power until it reaches a set target value; and in some embodiments it may include the amount of power delivered is performed using a proportional integral derivative controller.

As mentioned above, embodiments of the methods and devices provided here may make use of inductance in place of or in addition to resistivity as an electrical means by which to measure the size, the circumferential length for example, of an expandable operative element, and by inference, the circumference and related dimensions of a lumen in which the device has been place. Thus, for example, the method of measuring the size of a body lumen may include expanding an operative element within the lumen, the operative element having sensing circuitry with inductance that varies according to the size of the operative element, varying the sensing circuitry in accordance with the expansion of the operative element, measuring the inductance of the sensing circuitry, and determining the size of the lumen based on the measuring step.

By way of another example of using inductance as a size-measuring parameter of sensing circuitry, a device for measuring the size of a body lumen may include an expandable operative element including circuitry whose inductance varies according to the size of the operative element. By way of a further example of implementing inductance as an approach to sizing a body lumen in the context of an ablational treatment, a method for ablating targeted tissue in a body lumen may include inserting an operative element into the lumen, the operative element having sensing circuitry with inductance that varies according to the size of the operative element, expanding the operative element to contact the target tissue at a predetermined pressure, varying the sensing circuitry in accordance with the expansion of the operative element, measuring the inductance of the sensing circuitry, determining the size of the lumen based on the measuring step, and controlling the delivery of energy to the operative element according to the size of the lumen.

BRIEF DESCRIPTION OF THE DRAWINGS

FIG. 1A shows the support pulled away from the balloon to clarify that a portion of the support and an edge is adherent to the balloon, and another portion and its edge is not connected to the balloon.

FIG. 1B shows the operative element of the device with the non-adherent portion of the support furled around the balloon in a deployable configuration, the non-adherent portion and its edge overlapping around the adherent portion.

FIG. 1C shows the device of FIGS. 1A and 1B with an optional feature of the operative element 140, one or more elastic bands 180 wrapped around the electrode support 160.

FIG. 1D shows the device of FIG. 1C in a collapsed state, with balloon portion being uninflated (or deflated), this being the state of the device when it is being deployed into a lumen and being positioned at a target site, as well as the state of the device after delivering ablation energy and about to be removed from the lumen.

FIG. 2A is a view of the support in a circumferentially-contracted state, with extensive overlap between the inner-laying and outer-laying edges of the support.

FIG. 2B is a view of the support in a circumferentially-expanded state, with a small amount of overlap between the edges of the support.

FIG. 3A is a view of the support in a circumferentially-contracted state, with extensive overlap between the edges of the support.

FIG. 3B is a view of the support in a circumferentially-expanded state, with a small amount of overlap between the edges of the support.

FIG. 4A is a view of the support in a circumferentially-contracted state, with extensive overlap between the edges of the support.

FIG. 4B is a view of the support in a circumferentially-expanded state, with a small amount of overlap between the edges of the support.

FIG. 5A shows the balloon in a contracted state, with the support in a state of maximal overlap.

FIG. 5B shows a cross-sectional view of the balloon in a state of partial expansion, with the support in a state of partial overlap.

FIG. 5C shows a cross-sectional view of the balloon in a state of full expansion, with the support in a state of minimal overlap.

FIG. 6A shows the band of conductive elastomer in a state of minimal expansion, the ohmmeter displaying low resistivity.

FIG. 6B shows the band of conductive elastomer in a state of moderate expansion, the ohmmeter displaying mid-level resistivity.

FIG. 6C shows the band of conductive elastomer in a state of full expansion, the ohmmeter displaying high resistivity.

DETAILED DESCRIPTION OF THE INVENTION

Principles and General Considerations

Figure 1A:
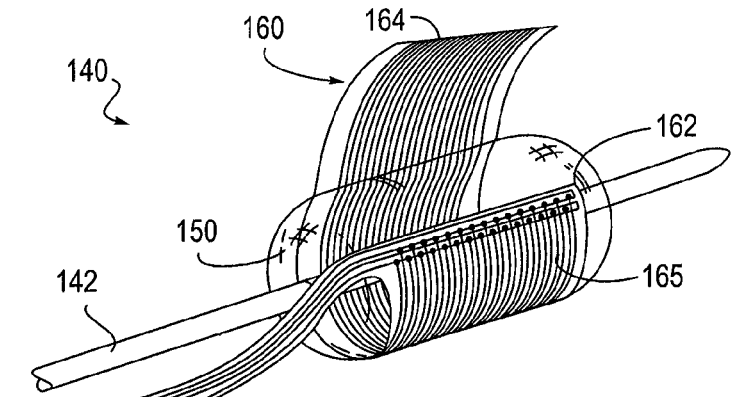
FIG. 1A-1D provide perspective views of an ablation device with an overlapping electrode support furled around an expandable balloon, the operative element including a balloon and an electrode support in an expanded state.

An object of this invention is to provide high-resolution measurements of the size of a body lumen in real time, when an ablative operational element is positioned in the lumen. The measurement relates most directly to the operative element itself, however, as the operative element fills the lumen upon its expansion, the measurement also reflects the size of the lumen. Body lumens are typically compliant and variable in size according to their contents or moment-to-moment physiological status, as lumens typically have no hard structural or immediately constraining features such as bone. The sizing methods provided herein thus focus on the size of the lumen, as reflected by the size of a space-filling operative element, in the moment as the operative element resides in the lumen, which is typically immediately prior to delivery of a form of therapy, such as ablational energy, from the operative element to the inner surface of the lumen. The fundamental parameter upon which these measurements are based includes resistivity of one or more size-sensing circuits, as the circuits are configured to provide an informative signal that relates to the size of the operational element filling the lumen. The size dimension being measured can relate to any of radius, diameter, or circumference, as all these values are interrelated, however the signal typically relates most directly to circumference. In addition to resistivity, other electrical parameters of the circuits that may be directed to this same object include inductance.

Two basic approaches to the measurement are provided by methods and devices provided herein. One approach relates to the use of a conductive elastomer arranged around the circumference, or a portion of the circumference of the expandable operative element. In this approach, a size-sensing circuit measures the resistivity of the operative element as changes shape, for example, as it expands or stretches. A second approach to measurements of expandable operative elements relates to the use of operative element embodiments that include slidably overlapping leaves as part of the mechanism by which they radially expand. These two approaches are described below, first in terms of the basic operating principles, structures, and methods, and then later, in the context of specific illustrated examples. Still further, these embodiments are described in the larger context of the use of these operative elements on ablation catheters.

In some embodiments of the invention, in accordance with the first approach noted above, an elastic element or elastomer is electrically-conductive, as provided by the use, for example by inclusion of silver-filled silicone. The resistivity of an electrically-conductive elastomer varies as a function of the extent to which the elastomer is stretched; when electrically-conductive elastomer is stretched, it has relatively high resistivity, and when contracted it has relatively low resistivity. Thus, by monitoring the resistivity of an electrically-conductive elastomer wrapped around an expanding balloon, a measure of the size (as exemplified by the circumference) of the balloon is provided. The system may be empirically calibrated prior to use in a body lumen, by testing resistivity as a function of the degree of expansion of the balloon, for example, when collapsed, and when at varying degrees of expansion to a state of the maximal expansion anticipated in normal use. Based on this information and other empirical information, these resistivity values permit estimates of the balloon diameter.

Some alternative embodiments of the invention make use of strain measurements to estimate the size of body lumen, such as an esophagus, prior to performing an ablation treatment. Elastic members such as bands may be wrapped around the edges of an expansion balloon, attached to the surface of the balloon such that when balloon is expanded, the elastic elements stretch to coincide with the expansion of the balloon. This balloon expansion forces the elastic member to elongate, which causes an increase in axial load to the elastic element between the attachment points of the elastic element-balloon interface, such load can be measured as strain which can in turn be related to size.

In alternative embodiments of the invention, instead of using a conductive elastomer, the elastic element may be attached to the operative element (or a portion thereof whose expansion relates to the expansion of the element as a whole) through an intermediary element used for measuring forces or strain. For example, a strain gauge element may be attached directly to the balloon and to the end of the elastic element. As the elastic element stretches it increases the strain on the strain gauge, and such strain data can be used to provide size information, which can be used in turn, to normalize the delivery of treatment to size parameters, such as luminal circumference or surface area.

In accordance with the second approach to device or lumen measurements as noted above, some embodiments of the invention include features that allow the operative element 140 to determine its own size, as its size varies by expanding and contracting within a body lumen, in preparation for the delivery of ablational energy. More specifically, the expansion state or size can be related to absolute dimensions of radius, diameter, or circumference. These values, derived from the operative element and associated size-sensing circuitry, can be related to the real time dimensions of the lumen at the site where the operative element is situated. More particularly, these dimensions, in combination with a longitudinal measure of a portion of a lumen, can all be related to the surface area of mutual contact between an ablational energy delivery element such as an array of radiofrequency electrodes and the target tissue. The object of knowing this surface area dimension is to enable the delivery of a specific power density (Watts/cm$^2$) or energy density (Joules/cm$^2$) to the tissue area that is targeted for ablation. In contrast to the pressure-based sizing balloon-based approach described in U.S. patent application Ser. No. 11/244,385 of Jackson (US Patent Pub. No. 2006/0095032), the approach described herein is based on resistivity or inductance of size-sensing circuits whose resistance varies according to the amount of overlap of electrode support edges.

As shown generally in FIGS. 2A-4C, as the diameter of the expandable balloon expands, the overlapping region 190 of the two ends of the unfurling ablational energy delivery element (radiofrequency electrodes being an exemplary ablational energy delivery element) support 160 decreases. Thus, the amount of surface area of the electrode support exposed to the tissue is inversely proportional to the overlapping surface of the electrode support. Described below in greater detail are various electrical approaches with which to estimate that overlapping surface area, and thereby estimate the area of tissue exposed to the ablational surface. Briefly, electrical contacts 170 are placed in the overlapping region 190 on both sides of the electrode support 160 within the overlapping region. The electrical contacts are configured in such a way that those that are able to form a complete circuit provide information that relates to the degree of overlap, and thus to the circumference of the operative element at that point in time.

In some embodiments of the invention, the size-sensing electrical contact points can be alternatively replaced with optical sensors, magnetics, or other electrical, electro-mechanical or optical means to determine the amount of electrode overlap. The opposing outward force of the balloon inflating from pressure with the constraining inward force from elastic members provides pressure that keeps the sensing elements in contact. Multiple circuits may be included within the system to provide redundancy, as for example to reduce the likelihood of the tissue or other material preventing physical contact between the two layers, or to provide multiple signals that can be integrated to provide higher resolution measurement. As another approach to protecting from interfering debris, the undersurface of the electrical contact points can include a metallic brush element to improve contact in the presence of tissue or other debris.

In other embodiments of the invention, rather than using resistive feedback, the inductive changes between the electrical circuit formed from contacts on the facing edges of the inner-laying and out-laying overlapping edges of the electrode support may be monitored. Inductance is a function of both the gap between the two circuits (it is desirable to keep as constant as possible) and the amount of overlap of the electrode/circuit areas.

Methods of estimating the surface area of luminal tissue with which electrodes are in contact include using measurements of electrical resistance with respect to tissue, and include the application of related Formulas 1 and 2, as described below.

$$R = \rho(L/A) \quad \text{Formula 1}$$

ρ=resistivity=1/electrical conductivity of the circuit. (This is an inherent function of electrode and wire compositions, and the conductivity of the tissue, the latter being different for each patient.)
L=length of the electrode
A=area of the electrode
R=resistance of electrode circuit Therefore, based on the Formula 1, to develop a predictable correlation between the electrode resistance and contact area, the following information is needed:

$$\text{Area in contact with tissue} = \rho(L/R) \quad \text{Formula 2}$$

Thus, to determine area, measurements of ρ and R are needed. The ρ estimate is obtained by measuring resistivity of the tissue, and an R estimate is obtained by measuring the starting resistance of the exposed circuit that is in contact with the tissue.

Typically, the manufacturing process by which embodiments of the invention are made includes specifications that provide a match between resistivity of size-sensing circuits and circumference of the operative element, such that these relationships are known. Manufacturing processes may also include quality control steps such that the relationship between resistivity of sensing circuits and circumference of the operating element at various levels of expansion is validated. In another approach to providing assurance of the validity of circumference measurements, an end-user can validate such measurements by checking individual operating elements with measurements of tubes of known dimension. By any of these approaches, when practicing the inventive method described herein, the expansion of an operative element to a predetermined pressure will yield a given resistivity that can be related to size of an operating element. According, in the practice of the method, it may be beneficial to use resistivity as a target value, and when using the operative element as a treatment device, the method can include expanding the operative element to achieve a given target or predetermined resistivity.

ILLUSTRATIVE EXAMPLES AND EMBODIMENTS

Turning now to illustrative examples of the approaches to measuring the internal dimension of a body lumen, embodiments of operative elements that that include an electrode support 160 that wraps overlappingly around an expandable balloon 150 and which provides a base from which size-sensing elements operate will be described first; embodiments that make use of an electrically conductive elastomer as a measuring element are described further below.

Figure 1B:
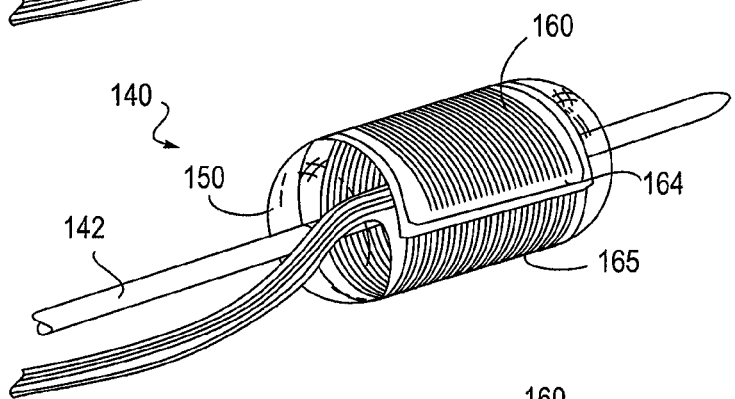
Figure 1C:
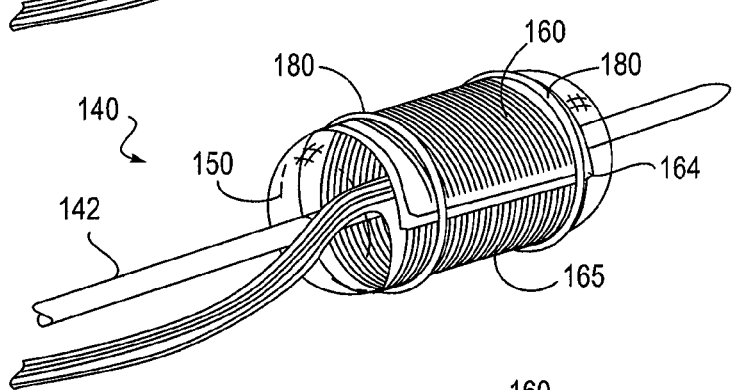
Figure 1D:
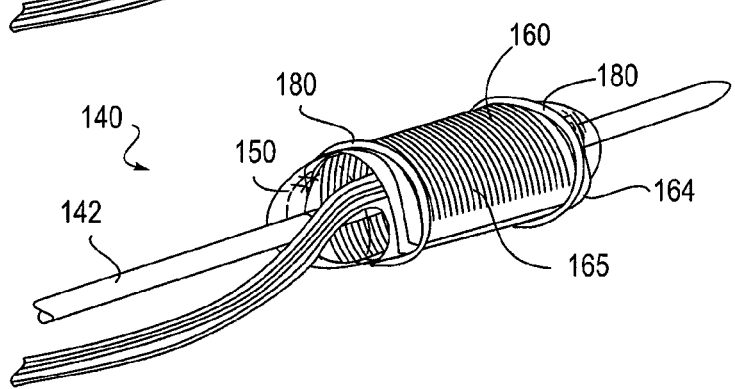

FIGS. 1A-1D provide perspective views of an ablation device 140 with an operative element 140 that includes overlapping electrode support 160 furled around an expandable balloon 150. An array of ablational energy delivery elements 165 such as radiofrequency electrodes is arranged on the exterior surface of the electrode support. The operative element is mounted on the distal end of an ablation catheter, of which the distal portion of a shaft 142 is seen, and around which the balloon 150 is configured. FIG. 1A shows the electrode support 160 pulled away from the balloon 150 to clarify that a portion of the support and an inner edge 162 is adherent to the balloon, and another portion and its outer edge 164 is not connected to the balloon. FIG. 1B shows the non-adherent portion of the electrode support 160 furled around the balloon 150 in a deployable configuration, the non-adherent portion and its edge overlapping around the adherent portion. FIG. 1C shows an optional feature of the operative element 140, one or more elastic bands 180 wrapped around the electrode support 160. In some embodiments, the elastic band 180 material is a conductive elastomer, as described in greater detail below, which can be included in a size-sensing circuit to provide information related to the degree of expansion of the operative element. FIG. 1D shows the device of FIG. 1C in a collapsed state, with balloon portion 150 being uninflated (or deflated), this being the state of the device when it is being deployed into a lumen and being positioned at a target site, as well as the state of the device after delivering ablation energy and about to be removed from the lumen.

Figure 2A:
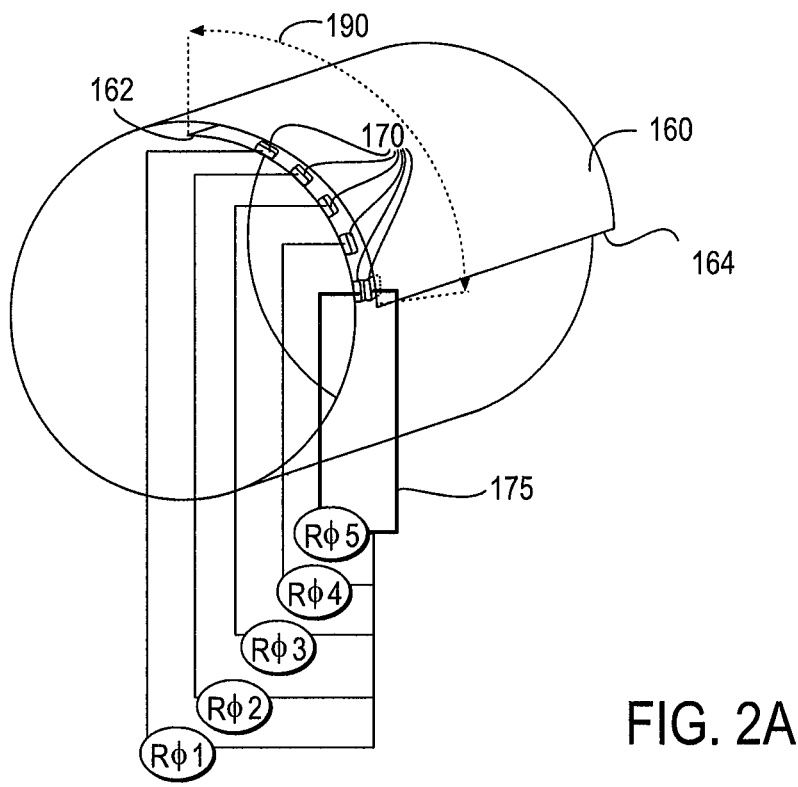
FIGS. 2A and 2B provide views of an embodiment of a circumferentially overlapping electrode support with a set of discrete measuring electrical contacts linearly arranged in a circumferential orientation on the outer aspect of an inner-laying edge of the support and a single contacting electrode on the inner aspect of the outer-laying edge of the support, the contacts within the area of mutual overlap on their respective edge.
Figure 2B:
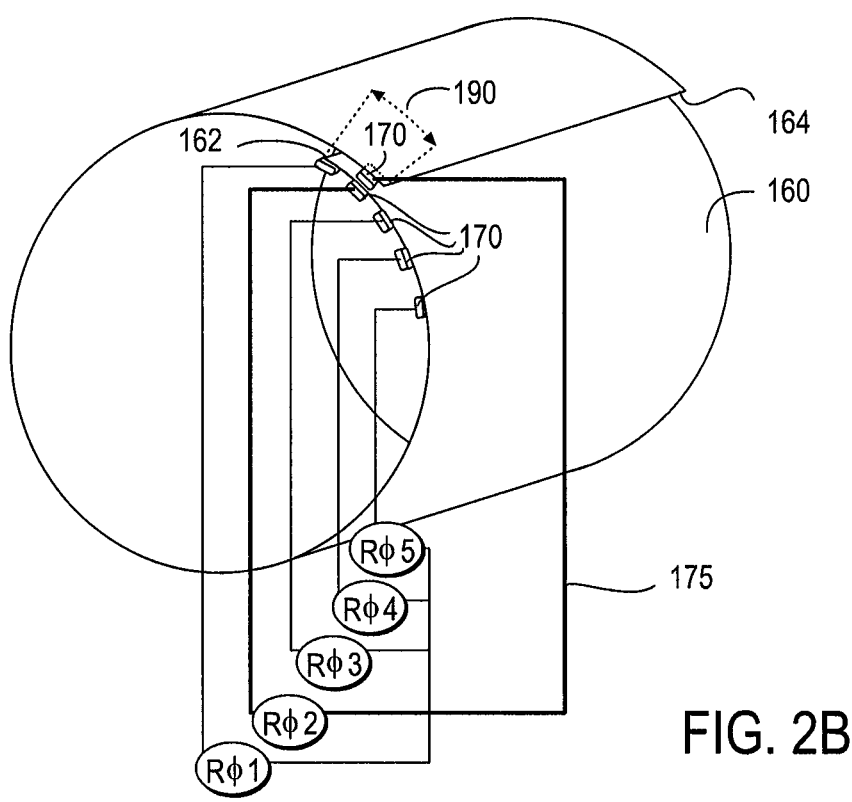

FIGS. 2A-6C focus on the overlapping electrode support 160, and the features that allow determination of the state of expansion of the support; not seen in these particular views is an expandable balloon 150 (see FIGS. 1A-1D) that resides internal to the support and which provides the expansive force. Thus, FIGS. 2A and 2B provide views of an embodiment of a circumferentially overlapping electrode support 160 with a set of discrete measuring electrical contacts 170 linearly arranged in a circumferential orientation on the outer aspect of an inner-laying edge 162 of the support 160 and a single contacting electrode 170 on the inner aspect of the outer-laying edge 164 of the support. The contacts on both edges of the support lie within the area of mutual overlap 190 on their respective edge. The number of sensing electrical contacts on inner-laying edge, in various embodiments, may vary typically between three and ten, but may include any appropriate number suitable for the dimensions of the contacts and the support. FIG. 2A shows the support 160 in a circumferentially-contracted state, with an extensive region of overlap 190 between the edges of the support. In this configuration, the circuit that is completed by connection between the sensing electrode on the outer-laying edge and the one sensing electrode of five possible electrodes is one that forms a circuit (bold line) with resistance R5. FIG. 2B shows the support 160 in a circumferentially-expanded state, with a small amount of overlap 180 between the edges of the support. In this configuration, the circuit that is completed by connection between the sensing electrode on the outer-laying edge and the one sensing electrode of five possible electrodes is one that forms a circuit (bold line) with resistance R2.

Another feature associated with the manner in which the inner-laying edge 162 and the outer-laying edge 164 of the energy-delivery support 160 interact involves their ability to slide past each other without disturbing the integrity or their generally flattened aspect; this feature derives from the stiffness of the material forming the support 160, and its general non-self sticking nature. Embodiments of the support 160 typically comprise a flexible, non-distensible backing, formed from a thin, rectangular sheet of polymer materials such as polyimide, polyester or other flexible thermoplastic or thermosetting polymer film. The support 160 may also comprise polymer covered materials, or other nonconductive materials. Additionally, the backing may include an electrically insulating polymer, with an electro-conductive material, such as copper, deposited onto a surface so that an electrode pattern can be etched into the material to create an array of electrodes. The slidability of the two longitudinal edges across each other is not particularly visible in FIGS. 1A-1C, however it is depicted in FIGS. 2A-5C. For example, the overlapping region 190 is comparatively large in FIGS. 2A, 3A, and 4A, and comparatively small in FIGS. 2B, 3B, and 4C, the change having occurred by the inner 162 and outer 164 edges having slid past each other. The slidability is of particular note in FIGS. 5A-5C, as in this embodiment an elastic band 180 surrounds the overlapping edges. The elastic band exerts a compressive force that urges the collapse of the operative element as the balloon deflates, but the overall balance of compressive force and the slidability of the overlapping edges is still one that allows slidability to prevail in spite of the compression being exerted by the elastic band.

Figure 3A:
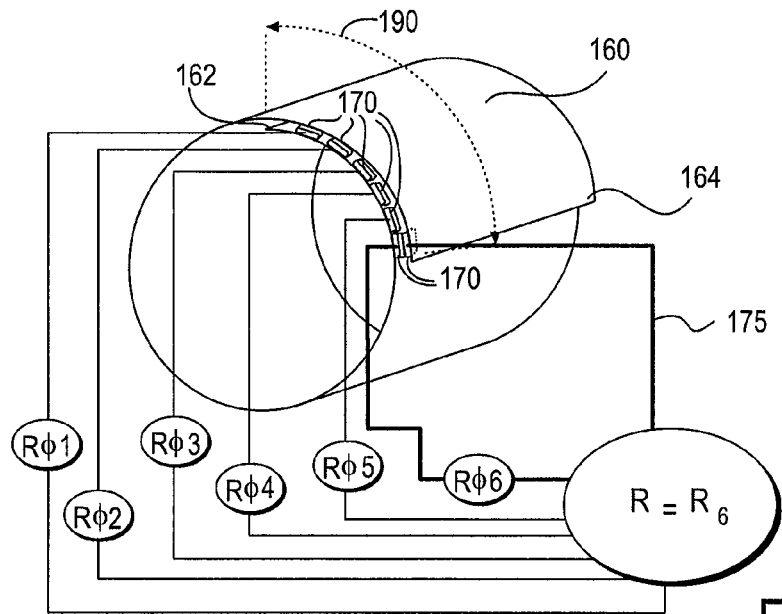
FIGS. 3A and 3B provide views of an embodiment of a circumferentially overlapping electrode support with a set of closely-spaced measuring electrical contacts linearly arranged in a circumferential orientation on the outer aspect of an inner-laying edge of the support and a single contacting electrode on the inner aspect of the outer-laying edge of the support, the contacts within the area of mutual overlap on their respective edge.
Figure 3B:
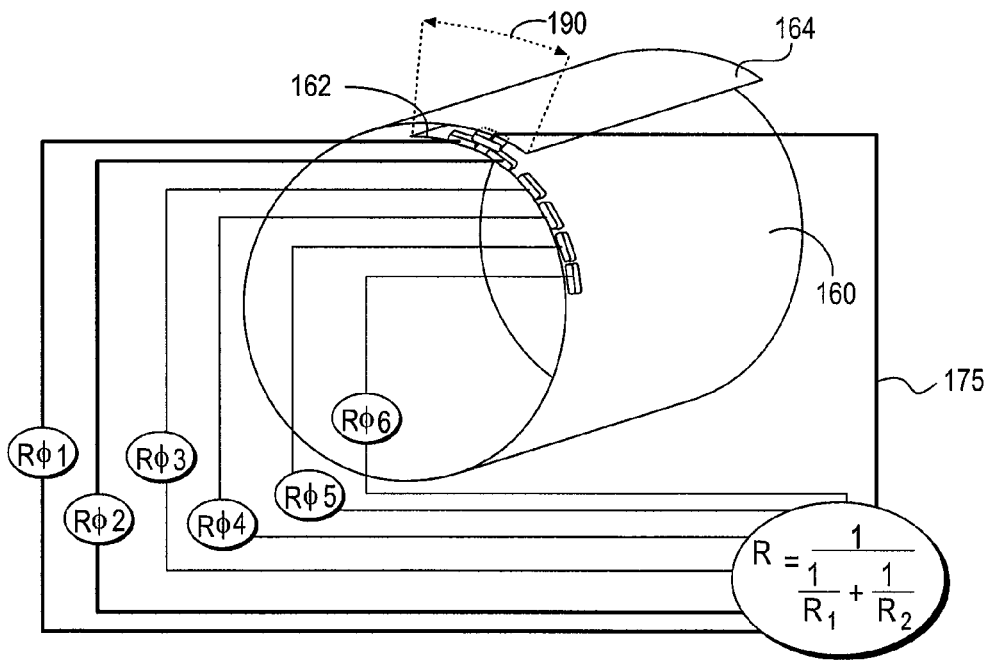

FIGS. 3A and 3B provide views of an embodiment of a circumferentially overlapping electrode support 160 with a set of closely-spaced measuring electrical contacts 170 linearly arranged in a circumferential orientation on the outer aspect of an inner-laying edge 162 of the support and a single contacting electrode 170 on the inner aspect of the outer-laying edge 164 of the support 160, the contacts within the area of mutual overlap 180 on their respective edge. FIG. 3A shows the support 160 in a circumferentially-contracted state, with extensive overlap between the two longitudinal edges of the support, while FIG. 3B shows the support 160 in a circumferentially-expanded state, with a small amount of overlap between the edges of the support. In FIG. 3A, the sensing electrode on the outer-laying edge is in contact with a single sensing electrode on the inner-laying edge that completes a circuit with a resistance R6. In FIG. 3B, the sensing electrode on the outer-laying edge is in contact with two adjacent sensing electrodes on the inner-laying edge which by themselves would form circuits with resistances of R1 and R2 respectively. In the circumstance, as illustrated, where the circuit formed includes both inner-laying sensing electrodes yield a circuit with a resistance, as noted in the figure, where R=1/(1/R1+1/R2). The difference between the embodiments depicted in FIGS. 2(A and B) vs. those in 3(A and B) is that the latter embodiment yields greater resolution or granularity in the circumferential measurement. Other dimensions of sensing electrodes being equal, the embodiment of FIG. 3 provides twice as many value points than are provided by the embodiment of FIG. 2. Resolution of measurements can also be generally understood as being a function of the number (or dimensions) of sensing electrodes distributed along the region of overlap 190.

Figure 4A:
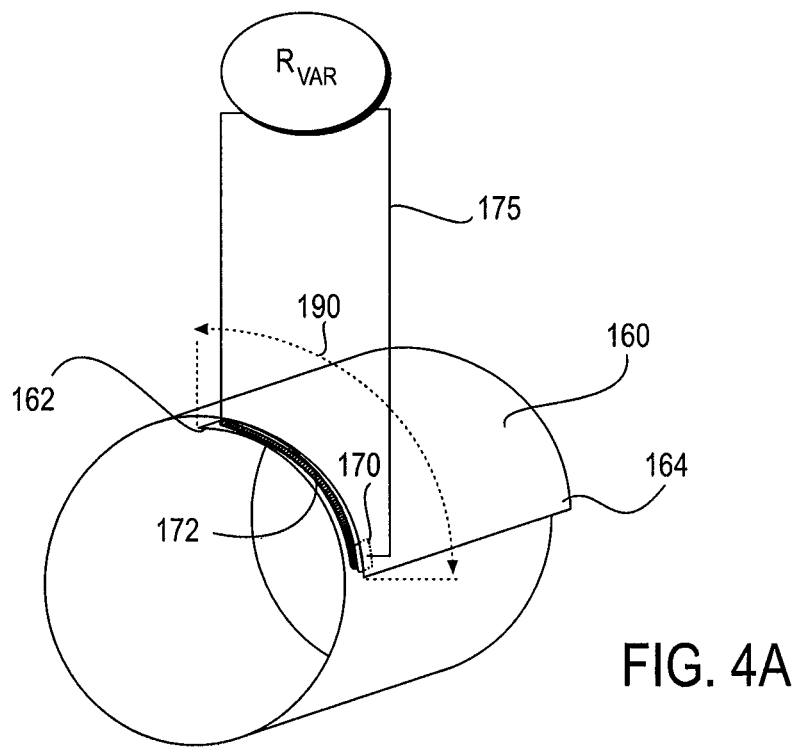
FIGS. 4A and 4B provide views of an embodiment of a circumferentially overlapping electrode support with a size-sensing circuit that includes a connection between an electrical contact on the inner aspect of an outer-laying edge and a site along the length of an electrode in the form of a conductive material linearly arranged in a circumferential orientation on the outer aspect of the inner-laying edge of the support, the contact occurring within the area of mutual overlap.
Figure 4B:
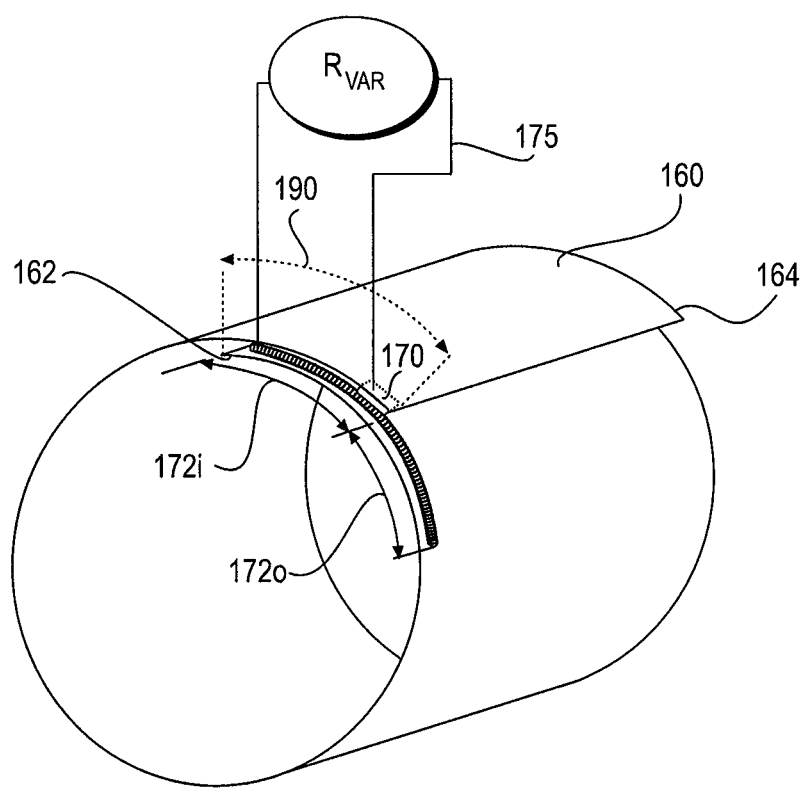

FIGS. 4A and 4B provide views of an embodiment of a circumferentially overlapping electrode support 160 with a size-sensing circuit 175 that includes a connection between an electrical contact on the inner aspect of an outer-laying edge 164 and a site along the length of an elongated sensing electrode 172 in the form of a conductive material linearly arranged in a circumferential orientation on the outer aspect of the inner-laying edge 162 of the support, the contact occurring within the area of mutual overlap 180. FIG. 4A shows the support 160 in a circumferentially-contracted state, with extensive overlap between the edges of the support, while FIG. 4B shows the support 160 in a circumferentially-expanded state, with a small amount of overlap between the edges of the support. In this expanded configuration, the elongated electrode 172 can be seen to functionally-divided into two segments, a portion of the electrode 172i is included within the circuit 175, and a portion of the electrode 172o is outside of the circuit. This situation differs from that of the elongated electrode 172 in the contracted configuration of the electrode support 160 as seen in FIG. 4A, where the whole of the electrode or where nearly the whole of the electrode is included within the circuit 175. Inasmuch as the resistivity of the circuit is increased by the length of the electrode included in the sensing circuit, the resistivity Rvar of the circuit 175 formed in FIG. 4A is relatively high, and the resistivity Rvar formed in FIG. 4B is relatively low. From such differences in resistivity (or inductance, in alternative embodiments), the sensing circuitry provides data that are informative with regard to the circumference of the support 160.

Figure 5A:
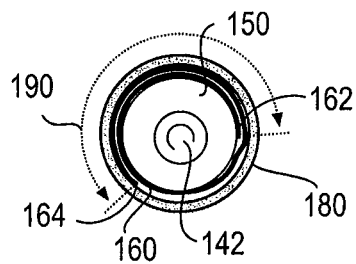
FIGS. 5A-5C show cross-sectional views of the deployable embodiment depicted in FIG. 4B with the balloon at varying levels of expansion, and they further depict an elastic band surrounding the furled support which urges collapse of the balloon and the slidable return of the overlapping edges to their state of maximal overlap.
Figure 5B:
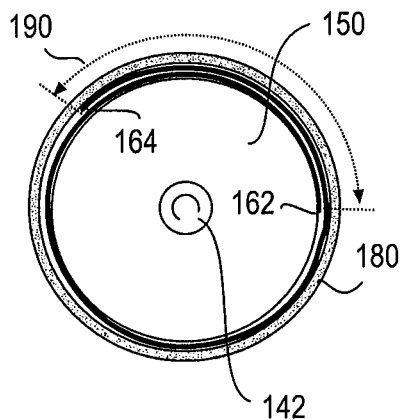
Figure 5C:
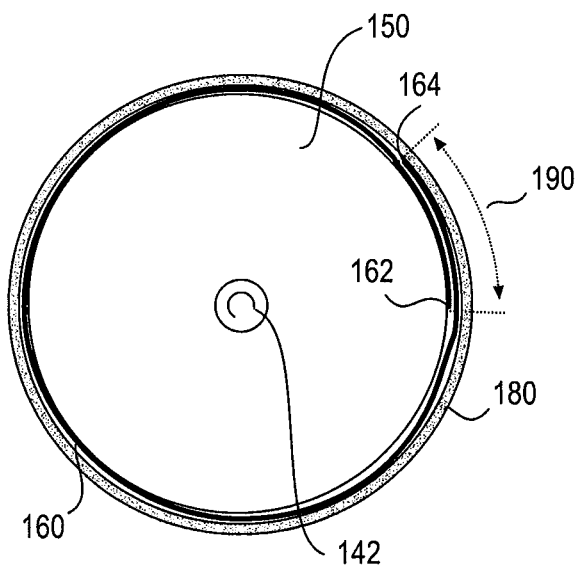

FIGS. 5A-5C show cross-sectional views of the deployable embodiment of an operative element depicted in FIG. 4B with the balloon 150 at varying levels of expansion, and they further depict an elastic band 180 surrounding the furled support 160 which urges collapse of the balloon and the slidable return of the overlapping edges to their state of maximal overlap. In some embodiments, this elastic band is formed from a conductive elastomer that can be included in a size-sensing circuit 175, as described below. FIG. 5A shows the balloon 150 in a contracted state, with the support in a state of maximal overlap. FIG. 5B shows a cross-sectional view of the balloon 150 in a state of partial expansion, with the support in a state of partial overlap. FIG. 5C shows a cross-sectional view of the balloon 150 in a state of full expansion, with the support in a state of minimal overlap.

Turning to some general considerations, FIGS. 2A-4B show embodiments in which the inner or center-facing aspect of the outer-laying edge 164 has a single electrical contact that makes contact and complete size-sensing circuits 175 with varying forms of electrodes on the outer-facing aspect of the inner laying edge 162 of overlapping edges of an electrode support 160. For the purposes of description it can be understood that the outer-laying edge 164 is a first edge of the support and that the inner-laying edge 162 is a second edge of the support. However, it can also be understood that the labels of first and second are arbitrary, and that further, in alternative embodiments, the distribution of electrodes between inner- and outer-laying support edges may reversed such that the outer-laying edge 164 is a second edge of the support and has multiple sensing electrodes, and the inner laying edge 162 is a first edge with a single sensing electrode, such configuration having no substantive difference between the function and the information related to the size-sensing circuitry.

Figure 6A:
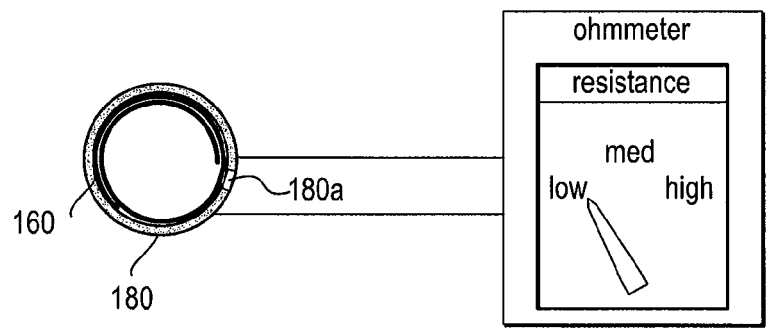
FIGS. 6A-6C provide schematic views of a band of conductive elastomer in various states of collapse to expansion, as in the configurations that would correspond to the embodiments depicted in FIGS. 5A-5C, with an ohmmeter measuring the resistivity at each state.
Figure 6B:
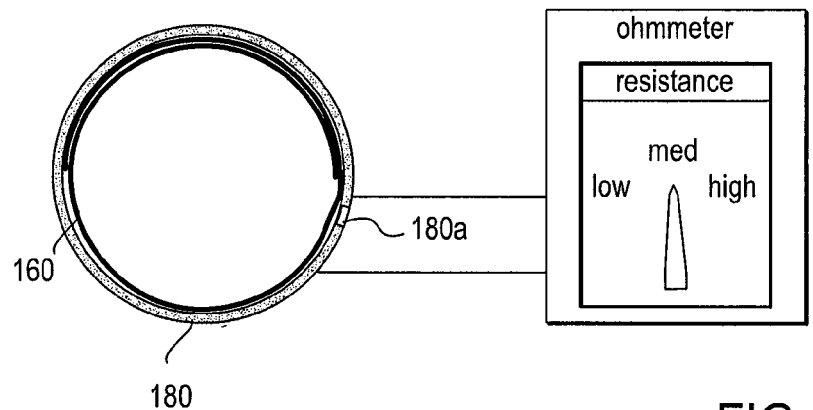
Figure 6C:
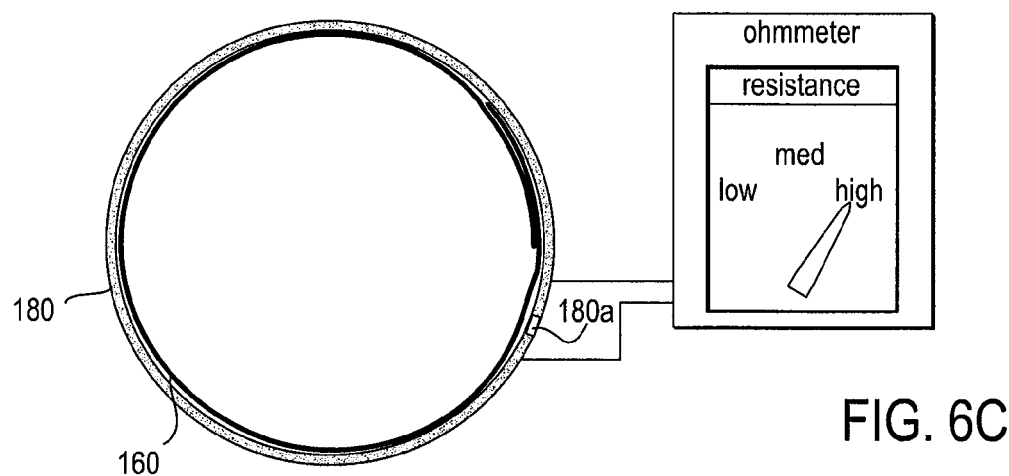

Turning now to illustrative examples of the approaches to measuring the internal dimension of a body lumen, embodiments of operative elements that that include a piece of conductive elastomer wrapped around the operative element will be described. FIGS. 6A-6C provide schematic views of a band of conductive elastomer 180 in various states ranging from minimal circumference to full or nearly-full circumferential expansion (as in the configurations that would correspond to the embodiments depicted in FIGS. 5A-5C) with an ohmmeter measuring the resistivity a sensing circuit 175 at each state of expansion. The conductive elastomeric band 180 includes a non-conductive gap 180a, the circuitry connecting to the conductive band on either side of the non-conductive gap. The composition of embodiments of the conductive elastomer includes conductive elements distributed within a polymeric matrix. When the polymeric matrix is in its preferred or fully contracted state, the absolute spatial density of the conductive elements is maximal, and consequently conductivity is maximal and resistivity is minimal. On the other hand, when the polymeric matrix is stretched, the spatial density of the conductive elements is diminished, conductivity decreases, and resistivity increases.

A circuit that includes a conductive elastomer arranged around an operative element in a manner such that the length of the elastomer reflects the degree of expansion of the circumference of the operative element thus provides a signal that can be related to the circumference of the operative element. FIG. 6A shows the band of conductive elastomer 180 in a state of minimal expansion, the ohmmeter displaying low resistivity. FIG. 6B shows the band of conductive elastomer 180 in a state of moderate expansion, the ohmmeter displaying mid-level resistivity. FIG. 6C shows the band of conductive elastomer 180 in a state of full expansion, the ohmmeter displaying high resistivity.

Two bands of conductive elastomer are shown in the operative element embodiment shown in FIG. 1C, one at either longitudinal end of the electrode support 160. The cross-sectional views provided in FIGS. 5A-5C and 6A-6C show a single band of conductive elastomer. Embodiments of the invention thus include those provided with one or more conductive elastomer bands. Further, the configuration of the conductive elastomer pieces may vary according to the practical needs of securing the electrode support, or securing or supporting, or otherwise constraining the expandable balloon. In some embodiments, the conductive elastomer may take the form of a web or a net. In some embodiments it need not necessarily embrace the full circumference of the operative element; embracing a representative partial expanse of an expandable circumference can be sufficient to derive circumferential sizing information. In addition to positioning the conductive elastomer on a surface exterior to an expanding portion of the operative element, in some embodiment, a conductive elastomer may be adhered to an inner surface of an expanding member such as a balloon. The only requirement in serving the object of the present invention is that the degree of linear stretch of the elastomer relates to the circumference of the operative element. Some embodiments of the invention may include both of the basic forms of resistivity sizing features as described herein, i.e., some embodiments may include circuits that include sections of size-sensing conductive elastomer, as described, as well as size-sensing circuits associated with the mutual area of overlap of overlapping expandable electrode supports. In such embodiments, algorithms may be employed to integrate separate sources of sizing information to yield an optimal result.

The provision of one or more bands of conductive elastomer 180 to provide information that relates directly to the circumference of an operative element is broadly applicable to many ablational operative elements that expand to make therapeutic contact with a body lumen. U.S. Pat. No. 7,150,745 of Stern et al. (incorporated herein, in its entirety), for example depicts embodiments of operative elements in FIGS. 2-4; further embodiments are shown in FIGS. 8-18. Each of these embodiments can be fitted with one or more conductive elastomeric bands 180, and thus are included as embodiments of the present invention.

Various of the ablational system and method embodiments provided in U.S. Pat. No. 7,150,745 of Stern also include an overlapping ablational energy delivery element support in which a region where the longitudinal edges of the support mutually overlap is related to the degree of circumferential expansion provided by an expandable mechanism configured within the circumferential space of the support. These embodiments include those depicted in FIGS. 14A and 14B, 15A-15C, 16, and 17 (of U.S. Pat. No. 7,150,745). FIG. 15C is an embodiment that varies from the others by having two such regions where longitudinal edges of supports overlap. Each of these operative elements can be fitted with electrodes that provide sizing information as depicted in FIGS. 2A-4C of the present disclosure, and thus are included as embodiments of the present invention.

U.S. Pat. No. 7,150,745 of Stern et al. (incorporated herein, in its entirety) further includes description of various configurations of ablational energy delivery elements in the form of electrode arrays that may be place on an expandable electrode support (see FIGS. 13a-14d of U.S. Pat. No. 7,150,745). All of these ablational energy delivery elements may be included on embodiments of operative elements and their overlapping electrode supports as described in this specification and are hereby included as embodiments of the present invention.

Typical embodiments of the device of the present invention include radiofrequency delivery elements as the means by which to distribute ablative energy into targeted luminal tissue. The radiofrequency elements may be monopolar or biopolar electrodes, an electrode array of any pattern, or solid-state circuitry. As described above, these elements may, in some embodiments be arranged directly on an inflatable member such as a balloon, and in other embodiments be arranged on an electrode support, which itself is engaged at least partially around a balloon. Although the exemplary embodiments described herein typically distribute radiofrequency energy delivered by appropriate means, some embodiments may make use of other forms of ablative energy and appropriate distribution elements, such as microwave energy emanating from an antenna, light energy emanating from photonic elements, thermal energy transmitted conductively from heated ablational structure surfaces or as conveyed directly to tissue by heated gas or liquid, or a heat-sink draw of energy, as provided by cryonic cooling of ablational structure surfaces, or as applied by direct cold gas or fluid contact with tissue.

U.S. patent application Ser. No. 12/114,628 of Kelly et al., entitled "Method and apparatus for gastrointestinal tract ablation for treatment of obesity", as filed on May 2, 2008 further includes embodiments of electrode arrays can effect a fractional ablation (see FIGS. 48A-54B); a fractional ablation being one in which a portion of the tissue within the target area is ablated and another portion is not significantly affected. The result of such partial or fractional ablation is depicted in FIG. 55 of the Kelly application (U.S. Ser. No. 12/114,628). All of these ablational energy delivery element arrays are compatible devices and methods for determining the dimensions of a body lumen site targeted for ablation as described in the present disclosure, and are hereby included as embodiments of the invention described herein.

U.S. Pat. No. 7,150,745 of Stern et al. further includes extensive description of a generator as a component of a larger system that controls the operation of an ablational operative element. More particularly the generator controls the delivery of power, such as radiofrequency power, to the operative element, for distribution therefrom into target tissue. Further factors that participate in controlling the delivery of energy or power from the operative element include the time-course over which energy is delivered, and the temperature and impedance of target tissue. A constancy in the rate of power delivery is provided by a proportional derivative controller, which increases power level, and thus inherently the voltage level, until power reaches a set target value. In one embodiment, the generator is adapted to control the amount of energy delivered to the tissue over time based on the measured diameter of the esophagus as provided by resistivity values from the size-sensing circuits described in this disclosure, and as depicted in FIGS. 2A-4B (for operative elements that include overlapping electrode supports), and in FIGS. 6A-6C, for operative elements that include conductive elastomeric circuits. Further, the generator can be adapted to normalize the density of energy delivered to the tissue over time based on the measured diameter of the esophagus so that equivalent energy densities, such that a predetermined level of energy per unit area of electrode surface area (Joules/cm$^2$) can be delivered to esophagi of differing diameters. In another embodiment, the generator is adapted to control the amount of power delivered to the tissue over time based on the measured diameter of the esophagus so that equivalent power densities, such that a predetermined and constant level of power per unit area of electrode surface area (Watts/cm$^2$) can be delivered to esophagi of differing diameters.

Figure 7:
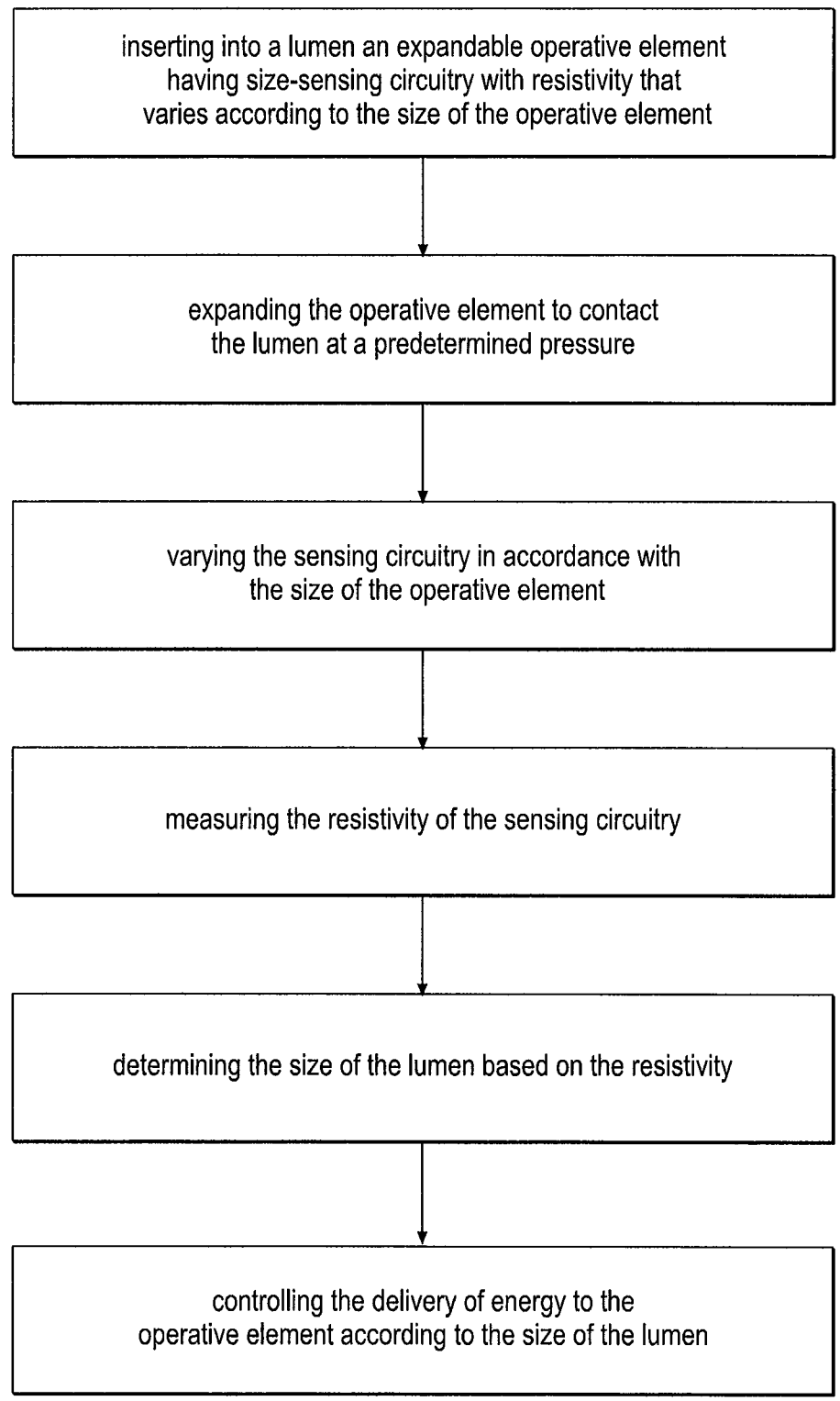
FIG. 7 provides a flow diagram of a method for ablational treatment that includes normalizing ablational energy per unit surface area of target tissue.

Embodiments of the present invention include a method for ablating tissue in a body lumen that normalizes ablational energy per unit surface area of target tissue, as shown in FIG. 7. The system makes use of size-sensing electrical circuits associated with the operative element of an ablative device to deliver information that inform a larger system overseeing the operative element of the size of the lumen about to receive ablative energy. The target tissue is typically abnormal, as for example columnar epithelium characteristic of Barrett's esophagus. However, the tissue itself may not necessarily be abnormal, as for example, ablation of apparently or presumptively normal tissue may serve a larger therapeutic purpose such as treating obesity (see, for example, the above-referenced U.S. patent application Ser. No. 12/114,628). The ablative method includes inserting an expandable operative element (with an expandable balloon, for example) an ablational energy delivery surface, and size-sensing circuitry with a resistivity that varies according to the circumference of the operative element into a lumen where targeted tissue is located, expanding the operative element to a predetermined pressure so as to contact a target site in the lumen, varying the sensing circuitry in accordance with the size of the operative element, measuring the resistivity of the circuitry associated with the operative element, relating or determining the resistivity to a value for the size (e.g., the circumference) of the operative element, and delivering an amount of ablational energy to achieve a predetermined level of energy delivery per unit surface area of abnormal tissue being ablated.

Devices and methods related to the present invention are described in detail in U.S. patent application Ser. No. 11/244, 385 of Jackson (US 2006/0095032), which specification, as noted above, is incorporated in its entirety into this application. That application describes the use of pressure and mass-flow information related to the influx of an expansion medium into an expandable balloon to derive sizing information. The present application also makes use of pressure information in order to allow the balloon to be inflated to a predetermined pressure. The appropriate pressure is one that varies over a range from about 1 psig to 7 psig, in some particular embodiments from about 3 psig to 5 psig and in some particular embodiments to a pressure of about 4 psig. This pressure, which may in some embodiments be determined on a case-by-case basis, but is more typically derived from general knowledge and experience with the target site. One of the factors underlying the rationale for the appropriate pressure includes the intention to effect a coaptive ablation, one in which the flow of blood into vessels of the region, capillaries in particular, is stopped by the local application of pressure from the expanded operative element, as described in U.S. patent application Ser. No. 11/244,385. Another aspect of the rationale for determining a target pressure to which balloon should be appropriately inflated relates to the compliance of the targeted lumen, i.e., the degree of change in circumference per unit outwardly applied pressure from within the lumen. These aspects of rationale thus underlie the step of the presently described method in which the balloon is inflated to a predetermined pressure, typically about 4 psig. In other embodiments of the invention that could be applied to other target sites, or to further another therapeutic objective, other pressures may be appropriately applied, and thus the use any appropriate pressure is included as an embodiment of the present invention.

Various terms have been used in the description to convey an understanding of the invention; it will be understood that the meaning of these various terms extends to common linguistic or grammatical variations or forms thereof. Terminology that is introduced at a later date that may be reasonably understood as a derivative of a contemporary term or designating of a subset of objects embraced by a contemporary term will be understood as having been described by the now contemporary terminology. While some theoretical considerations have been advanced in furtherance of providing an understanding of the invention the claims to the invention are not bound by such theory. For example, the level of pressure appropriate for inflating the balloon prior to the delivery of ablational energy is related by theory to the pressure in capillaries of the ablation site in order that a coaptive ablation may be effected. Moreover, any one or more features of any embodiment of the invention can be combined with any one or more other features of any other embodiment of the invention, without departing from the scope of the invention. Further, it should be understood that while these inventive methods and devices have been described as providing therapeutic benefit to the esophagus by way of example, such devices and embodiments may also have therapeutic application in other lumen or cavity sites within the body. Still further, it should be understood that the invention is not limited to the embodiments that have been set forth for purposes of exemplification, but is to be defined only by a fair reading of claims that are appended to the patent application, including the full range of equivalency to which each element thereof is entitled.

The invention claimed is:

1. A device for treating a body lumen comprising: an expandable operative element including an inflatable balloon and an ablation energy delivery element support arranged on an exterior of the inflatable balloon; and a sensing circuitry mounted to the support, wherein a resistivity of the sensing circuitry varies according to an amount of expansion of the inflatable balloon.

2. The device of claim 1, wherein the operative element further includes an ablative energy delivery element.

3. The device of claim 2, wherein the ablative energy delivery element includes any of a radiofrequency electrode, a radio frequency electrode array, or solid-state circuitry.

4. The device of claim 1, wherein the sensing circuitry comprises a portion of a band of conductive elastomer wrapped around the operative element such that when the inflatable balloon is contracted a length of the conductive elastomer band is also contracted, and when the inflatable balloon is expanded, the length of the conductive elastomeric band is stretched.

5. The device of claim 1, wherein the ablation energy delivery element support comprises a longitudinal first edge and a second longitudinal edge that overlap each other to form an area of mutual overlap.

6. The device of claim 5, wherein the support is circumferentially expandable by the balloon such that the area of mutual overlap is inversely related to the amount of expansion of the balloon.

7. The device of claim 5, wherein the sensing circuitry comprises sensing elements on both longitudinal edges of the ablational energy delivery element support in the area of mutual overlap, such elements configured to connect across the area of mutual overlap to form a circuit with a particular resistivity, the elements further configured such that the connection formed between sensing elements varies according to an amount of mutual overlap of the two longitudinal edges.

8. The device of claim 7, wherein the first edge includes a single sensing element and the second edge includes a plurality of spaced-apart sensing elements, the particular element among the plurality of elements on the second edge that connects to the element on the first edge varying according to an amount of mutual overlap of the two edges, the resistivity of the circuit formed varying according to the particular element on the second edge that is included in the circuit.

9. The device of claim 7, wherein the first edge includes a single sensing element and the second edge includes a plurality of closely-spaced sensing elements, the elements configured such that the element on the first edge connects with one of the plurality of the elements on the second edge or with a pair of adjacent elements on the second edge, the resistivity of the circuit formed varying according to which of the one or which adjacent pair of the elements on the second edge is included in the circuit.

10. The device of claim 7, wherein the first edge includes a single sensing element and the second edge includes an elongated sensing element, the elements configured such that the single element on the first edge forms a circuit by connecting with the elongated element on the second edge at a point that varies along the length of the elongated element thereby creating a circuit of varying length, the resistivity of the circuit formed varying according to the length of the element on the second edge that is included in the circuit.

11. The device of claim 1, wherein the ablation energy delivery element support is furled around the inflatable balloon in a deployable configuration.

12. The device of claim 1, wherein the operative element is configured for delivery of energy to tissue at a target tissue area.

* * * * *